United States Patent
Stölting et al.

(10) Patent No.: US 7,034,156 B2
(45) Date of Patent: Apr. 25, 2006

(54) METHOD FOR THE PRODUCTION OF 1-AMINO-3-PHENYLURACIL DERIVATIVES

(75) Inventors: Jörn Stölting, Köln (DE); Dorothee Hoischen, Düsseldorf (DE); Roland Andree, Langenfeld (DE); Karl-Heinz Linker, Leverkusen (DE); Holger Weintritt, Langenfeld (DE); Heinz-Jürgen Wroblowsky, Langenfeld (DE)

(73) Assignee: Bayer CropScience AG, Monheim (DE)

( * ) Notice: Subject to any disclaimer, the term of this patent is extended or adjusted under 35 U.S.C. 154(b) by 344 days.

(21) Appl. No.: 10/476,941

(22) PCT Filed: Apr. 25, 2002

(86) PCT No.: PCT/EP02/04610

§ 371 (c)(1),
(2), (4) Date: Nov. 6, 2003

(87) PCT Pub. No.: WO02/090338

PCT Pub. Date: Nov. 14, 2002

(65) Prior Publication Data

US 2004/0147400 A1    Jul. 29, 2004

(30) Foreign Application Priority Data

May 8, 2001  (DE)  .................. 101 22 235

(51) Int. Cl.
*C07D 239/54* (2006.01)
(52) U.S. Cl. ............. 544/311; 544/309; 544/310; 544/312; 544/313
(58) Field of Classification Search ........... 544/309, 544/310, 311, 312, 313
See application file for complete search history.

(56) References Cited

FOREIGN PATENT DOCUMENTS

WO   WO 98/27068   *   6/1998

* cited by examiner

*Primary Examiner*—Deepak Rao
(74) *Attorney, Agent, or Firm*—Richard E.L. Henderson

(57) ABSTRACT

The present invention relates to a novel process for preparing known 1-amino-3-phenyluracil derivatives, to novel 1-amino-6-hydroxy-3-phenyldihydro-2,4(1H,3H)pyrimidinedione derivatives of the formula (II)

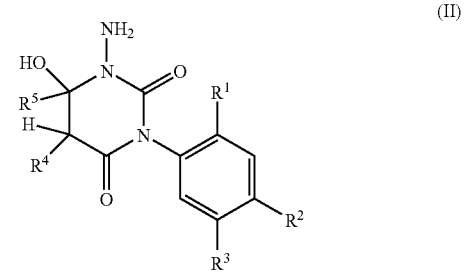

in which
$R^1$ is hydrogen, cyano, nitro or halogen,
$R^2$ is cyano, nitro, halogen or optionally substituted alkyl or alkoxy,
$R^3$ is hydrogen, hydroxyl, mercapto, amino, hydroxyamino, hydrazino, halogen, or one of the radicals —$R^6$, -Q-$R^6$, —NH—$R^6$, —NH—O—$R^6$, —NH—$SO_2$—$R^6$, —N($SO_2$—$R^6)_2$, —$CQ^1$-$R^6$, —$CQ^1$-$Q^2$-$R^6$, —$CQ^1$-NH—$R^6$, -$Q^2$-$CQ^1$-$R^6$, —NH—$CQ^1$-$R^6$, —N($SO_2$—$R^6$)($CQ^1$-$R^6$), -$Q^2$-$CQ^1$-$Q^2$-$R^6$, —NH—$CQ^1$-$Q^2$-$R^6$ or -$Q^2$-$CQ^1$-NH—$R^6$,
where
Q is O, S, SO or $SO_2$,
$Q^1$ and $Q^2$ are each independently oxygen or sulphur and
$R^6$ is optionally substituted alkyl, alkenyl, alkynyl, cycloalkyl, cycloalkylalkyl, aryl, arylalkyl, heterocyclyl or heterocyclylalkyl,
$R^4$ is hydrogen, halogen or optionally substituted alkyl, and
$R^5$ is fluorine- and/or chlorine-substituted alkyl,
as intermediates for the 1-amino-3-phenyluracil derivatives, and to a process for preparing the intermediates.

17 Claims, No Drawings

METHOD FOR THE PRODUCTION OF 1-AMINO-3-PHENYLURACIL DERIVATIVES

The present patent application has been filed under 35 U.S.C. 371 as a national stage application of PCT/EP02/04610, filed Apr. 25, 2002, which was published in German as International Patent Publication WO 02/090,338 on Nov. 14, 2002, which is entitled to the right of priority of German Patent Application 101 22 235.1, filed May 8, 2001.

The present invention relates to a novel process for preparing known 1-amino-3-phenyluracil derivatives (1-amino-3-phenyl-2,4(1H,3H)pyrimidinedione derivatives) and novel 1-amino-6-hydroxy-3-phenyldihydro-2,4(1H,3H)pyrimidinedione derivatives as intermediates therefore and to a process for preparing them.

It has already become known that certain 3-amino-1-phenyluracils can be prepared by reacting amino alkenoic esters with substituted phenylisocyanates or with substituted phenylurethanes in the presence of bases and reacting the resulting 1-phenyluracils with 1-aminooxy-2,4-dinitrobenzene (cf. EP-A-648 749, U.S. Pat. Nos. 5,593,945, 5,681,794, 6,110,870, WO-A-95/29168, U.S. Pat. Nos. 5,759,957, 5,962,372). However, a disadvantage of this process is that the desired products occur in relatively low yields and not always in sufficient quality. Also, the starting materials required have little suitability for the preparation on the industrial scale.

It is further already known that certain 1,3-oxazine-2,4(3H)diones which are unsubstituted on the nitrogen atom react with hydrazine to give uracils which bear an amino group as substituents. In contrast, the corresponding reaction of 1,3-oxazine-2,4(3H)diones which are substituted on the nitrogen atom results not in uracils but only pyrazole derivatives (cf. J. Heterocycl. Chem. 15 (1978), 1475–1478).

Finally, it is already known that 3-amino-1-phenyluracil derivatives can also be obtained by reacting substituted phenyloxazinediones with hydrazine hydrate or with acid adducts of hydrazine (cf. WO-A-98/27068). However, the yield and quality of the products obtained in this way are not entirely satisfactory.

It has now been found that 1-amino-3-phenyluracil derivatives (1-amino-3-phenyl-2,4(1H,3H)pyrimidinedione derivatives) of the general formula (I)

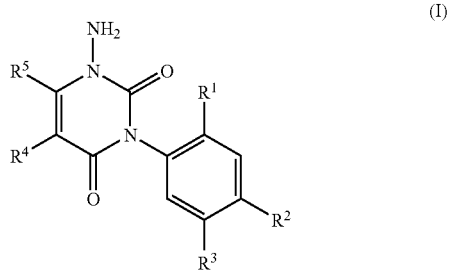

(I)

in which

R$^1$ is hydrogen, cyano, nitro or halogen,

R$^2$ is cyano, nitro, halogen or optionally substituted alkyl or alkoxy,

R$^3$ is hydrogen, hydroxyl, mercapto, amino, hydroxyamino, hydrazino, halogen, or one of the radicals —R$^6$, -Q-R$^6$, —NH—R$^6$, —NH—O—R$^6$, —NH—SO$_2$—R$^6$, —N(SO$_2$—R$^6$)$_2$, —CQ$^1$-R$^6$, —CQ$^1$Q$^2$-R$^6$, —CQ$^1$-NH—R$^6$, Q$^2$-CQ$^1$-R$^6$, —NH—CQ$^1$-R$^6$, —N(SO$_2$—R$^6$)(CQ$^1$-R$^6$), -Q$^2$-CQ$^1$-Q$^2$-R$^6$, —NH—CQ$^1$-Q$^2$-R$^6$ or -Q$^2$-CQ$^1$-NH-R$^6$, where Q is O, S, SO or SO$_2$, Q$^1$ and Q$^2$ are each independently oxygen or sulphur and R$^6$ is optionally substituted alkyl, alkenyl, alkinyl, cycloalkyl, cycloalkylalkyl, aryl, arylalkyl, heterocyclyl or heterocyclylalkyl, R$^4$ is hydrogen, halogen or optionally substituted alkyl, and R$^5$ is fluorine- and/or chlorine-substituted alkyl, by reacting 1-amino-6-hydroxy-3-phenyldihydro-2,4(1H,3H)pyrimidinedione derivatives of the general formula (II)

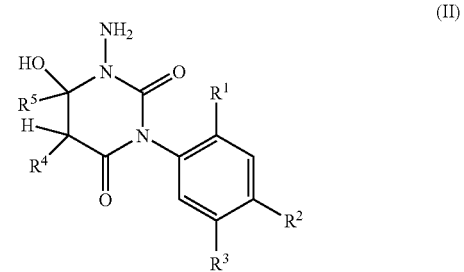

(II)

in which

R$^1$, R$^2$, R$^3$, R$^4$ and R$^5$ are each as defined above are reacted with a dehydrating agent, optionally in the presence of one or more reaction assistants and optionally in the presence of one or more diluents, at temperatures between −30° C. and +180° C.

Preferred definitions of the radicals and groups present in formula (I) are defined hereinbelow.

R$^1$ is preferably hydrogen, cyano, nitro, fluorine, chlorine or bromine,

R$^2$ is preferably cyano, nitro, fluorine, chlorine, bromine or optionally fluorine- and/or chlorine-substituted alkyl or alkoxy having 1 to 4 carbon atoms, R$^3$ is preferably hydrogen, hydroxyl, mercapto, amino, hydroxyamino, halogen, or one of the radicals —R$^6$, -Q-R$^6$, —NH—R$^6$, —NH—O—R$^6$, —NH—SO$_2$—R$^6$, —N(SO$_2$—R$^6$)$_2$, —CQ$^1$-R$^6$, —CQ$^1$-Q$^2$-R$^6$, —CQ$^1$-NH—R$^6$, -Q$^2$-CQ$^1$-R$^6$, —NH—CQ$^1$-R$^6$, —N(SO$_2$—R$^6$)(CQ$^1$-R$^6$), -Q$^2$-CQ$^1$-Q$^2$-R$^6$, —NH—CQ$^1$-Q$^2$-R$^6$ or -Q$^2$-CQ$^1$-NH-R$^6$, Q is preferably O, S or SO$_2$, Q$^1$ and Q$^2$ are preferably each oxygen.

R$^4$ is preferably hydrogen, fluorine, chlorine, bromine or optionally fluorine- and/or chlorine-substituted alkyl having 1 to 6 carbon atoms.

R$^5$ is preferably fluorine- and/or chlorine-substituted alkyl having 1 to 6 carbon atoms.

R$^6$ is preferably optionally cyano-, halogen-, C$_1$–C$_4$-alkoxy-, C$_1$–C$_4$-alkylthio-, C$_1$–C$_4$-alkylcarbonyl-, C$_1$–C$_4$-alkoxycarbonyl- or C$_1$–C$_4$-alkylaminocarbonyl-substituted alkyl having 1 to 6 carbon atoms, or optionally cyano-, carboxy-, halogen-, C$_1$–C$_4$-alkylcarbonyl-, C$_1$–C$_4$-alkoxycarbonyl- or C$_1$–C$_4$-alkylaminocarbonyl-substituted alkenyl or alkinyl each having 2 to 6 carbon atoms, or optionally cyano, carboxy, halogen, C$_1$–C$_4$-alkylcarbonyl- or C$_1$–C$_4$-alkoxycarbonyl-substituted cycloalkyl or cycloalkylalkyl each having 3 to 6 carbon atoms in the cycloalkyl group and optionally 1 to 4 carbon atoms in the alkyl moiety, or optionally mono- to tri-hydroxy-, -mercapto-, -amino-, -cyano-, -carboxy-, -carbamoyl-, -thiocarbamoyl-, —$C_1$–$C_4$-alkyl-, —$C_1$–$C_4$-haloalkyl-, —$C_1$–$C_4$-alkoxy-, —$C_1$–$C_4$-haloalkoxy-, —$C_1$–$C_4$-alkylthio-, —$C_1$–$C_4$-haloalkylthio-, —$C_1$–$C_4$-alkylsulphinyl-, —$C_1$–$C_4$-alkylsulphonyl-, —$C_1$–$C_4$-alkylamino- and/or -dimethylamino-substituted aryl or arylalkyl each having 6 or 10 carbon atoms in the aryl group and optionally 1 to 4 carbon atoms in the alkyl moiety, or optionally mono- to tri-hydroxy-, -mercapto-, -amino-, -cyano-, -carboxy-, -carbamoyl-, -thiocarbamoyl-, —$C_1$–$C_4$-alkyl-, —$C_1$–$C_4$-haloalkyl-, —$C_1$–$C_4$-alkoxy-, —$C_1$–$C_4$-haloalkoxy-, —$C_1$–$C_4$-alkylthio-, —$C_1$–$C_4$-haloalkylthio-, —$C_1$–$C_4$-alkylsulphinyl-, —$C_1$–$C_4$-alkylsulphonyl-, —$C_1$–$C_4$-alkylamino- and/or -dimethylamino-substituted heterocyclyl or heterocyclylalkyl having 2 to 6 carbon atoms and 1 to 3 nitrogen atoms and/or 1 or 2 oxygen atoms and/or one sulphur atom in the heterocyclyl group and optionally 1 to 4 carbon atoms in the alkyl moiety.

$R^1$ is more preferably hydrogen, fluorine or chlorine.

$R^2$ is more preferably cyano, fluorine, chlorine, bromine, methyl or trifluoromethyl.

$R^3$ is more preferably hydroxyl, mercapto, amino, fluorine, chlorine, bromine or one of the radicals —$R^6$, -Q-$R^6$, —NH—$R^6$, —NH—O—$R^6$, —NH—$SO_2$—$R^6$, —N($SO_2$—$R^6$)$_2$, —$CQ^1$-$R^6$, —$CQ^1$-$Q^2$-$R^6$, —$CQ^1$-NH—$R^6$, -$Q^2$-$CQ^1$-$R^6$, —NH—$CQ^1$-$R^6$, —N($SO_2$—$R^6$)($CQ^1$-$R^6$), -$Q^2$-$CQ^1$-$Q^2$-$R^6$, —NH—$CQ^1$-$Q^2$-$R^6$ or -$Q^2$-$CQ^1$-NH-$R^6$.

Q is more preferably O or $SO_2$.

$R^4$ is more preferably hydrogen, fluorine, chlorine, bromine, methyl, ethyl or trifluoromethyl.

$R^5$ is more preferably trifluoromethyl, chlorodifluoromethyl, fluorodichloromethyl or pentafluoroethyl.

$R^6$ is more preferably optionally cyano-, fluorine-, chlorine-, methoxy-, ethoxy-, methylthio-, ethylthio-, acetyl-, propionyl-, methoxycarbonyl-, ethoxycarbonyl-, methylaminocarbonyl- or ethylaminocarbonyl-substituted methyl, ethyl, n- or i-propyl, n-, i- or s-butyl, or optionally cyano-, carboxy-, fluorine-, chlorine-, bromine-, acetyl-, propionyl-, n- or i-butyroyl-, methoxycarbonyl-, ethoxycarbonyl-, n- or i-propoxycarbonyl-, methylaminocarbonyl-, ethylaminocarbonyl-, n- or i-propylaminocarbonyl-substituted propenyl, butenyl, propinyl or butinyl, or optionally cyano-, carboxy-, fluorine-, chlorine-, bromine-, acetyl-, propionyl-, methoxycarbonyl- or ethoxycarbonyl-substituted cyclopropyl, cyclobutyl, cyclopentyl, cyclohexyl, cyclopropylmethyl, cyclobutylmethyl, cyclopentylmethyl or cyclohexylmethyl, or optionally mono- to tri-hydroxy-, -mercapto-, -amino-, -cyano-, -carboxy-, -carbamoyl-, -thiocarbamoyl-, -methyl-, -ethyl-, -trifluoromethyl-, -methoxy-, -ethoxy-, -difluoromethoxy-, -trifluoromethoxy-, -methylthio-, -ethylthio-, -difluoromethylthio-, -trifluoromethylthio-, -methylsulphinyl-, -ethylsulphinyl-, -methylsulphonyl-, -methylamino-, -ethylamino- and/or -dimethylamino-substituted phenyl, benzyl or phenylethyl, or optionally mono- or di-hydroxy-, -mercapto-, -amino-, -cyano-, -carboxy-, -carbamoyl-, -thiocarbamoyl-, -methyl-, -ethyl-, -n- or -i-propyl-, -n-, -i-, -s- or -t-butyl-, -difluoromethyl-, -dichloromethyl-, -trifluoromethyl-, -trichloromethyl-, -chlorodifluoromethyl-, -fluorodichloromethyl-, -methoxy-, -ethoxy-, -difluoromethoxy-, -trifluoromethoxy-, -methylthio-, -ethylthio-, -difluoromethylthio-, -trifluoromethylthio-, -methylsulphinyl-, -ethylsulphinyl-, -methylsulphonyl-, -ethylsulphonyl-, -methylamino-, -ethylamino- and/or -dimethylamino-substituted heterocyclyl or heterocyclylalkyl from the group of oxiranyl, oxetanyl, furyl, tetrahydrofuryl, dioxolanyl, thienyl, tetrahydrothienyl, pyrrolyl, pyrazolyl, imidazolyl, triazolyl, oxazolyl, isoxazolyl, thiazolyl, isothiazolyl, oxadiazolyl, thiadiazolyl, pyridinyl, pyrimidinyl, triazinyl, pyrazolylmethyl, furylmethyl, thienylmethyl, oxazolylmethyl, isoxazolylmethyl, thiazolylmethyl, pyridinylmethyl, pyrimidinylmethyl, Surprisingly, the 1-amino-3-phenyluracil derivatives (1-amino-3-phenyl-2,4(1H,3H)-pyrimidinedione derivatives) of the general formula (I) can be prepared by the process according to the invention in considerably better yields and in higher purity than by the processes known hitherto.

The process according to the invention is notable for a series of advantages. For instance, the starting materials required are obtainable in a simple manner and also in relatively large amounts. In addition, carrying out the reaction according to the invention and the isolation of the desired substances presents no problems worthy of mention.

When the starting material used is 1-amino-3-(4-cyano-2,5-difluorophenyl)dihydro-6-hydroxy-6-trifluoromethyl-2,4(1H,3H)pyrimidinedione and the dehydrating agent used is oxalyl chloride, the course of the process according to the invention can be outlined by the following scheme:

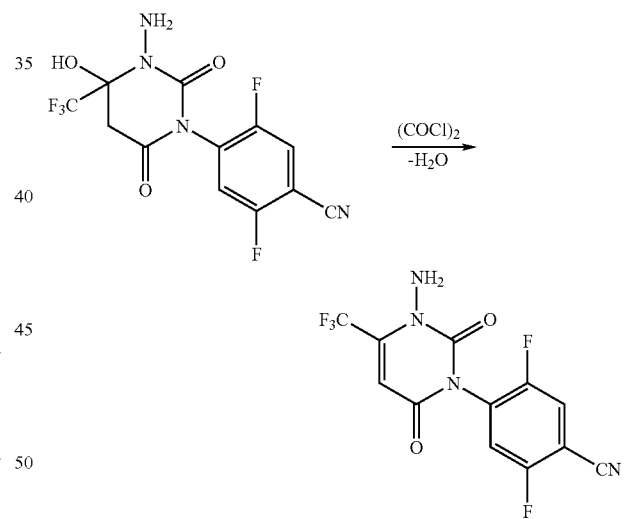

The 1-amino-6-hydroxy-3-phenyldihydro-1,4(1H,3H)-pyrimidinedione derivatives required as starting materials when carrying out the process according to the invention are generally defined by formula (II). Preference is given to using compounds of the formula (II) in which $R^1$ is hydrogen, cyano, nitro, fluorine, chlorine or bromine, $R^2$ is cyano, nitro, fluorine, chlorine, bromine or optionally fluorine- and/or chlorine-substituted alkyl or alkoxy having 1 to 4 carbon atoms, $R^3$ is hydrogen, hydroxyl, mercapto, amino, hydroxyamino, halogen, or one of the radicals —$R^6$, -Q-$R^6$, —NH—$R^6$, —NH—O—$R^6$, —NH—$SO_2$—$R^6$, —N($SO_2$—$R^6$)$_2$, —$CQ^1$-$R^6$, —$CQ^1$-$Q^2$-$R^6$, —$CQ^1$-NH—$R^6$, -$Q^2$-$CQ^1$-$R^6$, —NH—CQ$^1$-R$^6$, —N(SO$_2$—R$^6$)(CQ$^1$-R$^6$), -Q$^2$-CQ$^1$-Q$^2$-R$^6$, —NH—CQ$^1$-Q$^2$-R$^6$ or -Q$^2$-CQ$^1$-NH-R$^6$,
where
Q is O, S, SO or SO$_2$,
Q$^1$ and Q$^2$ are each independently oxygen or sulphur and
R$^6$ is optionally cyano-, halogen-, C$_1$–C$_4$-alkoxy-, C$_1$–C$_4$-alkylthio-, C$_1$–C$_4$-alkylcarbonyl-, C$_1$–C$_4$-alkoxycarbonyl- or C$_1$–C$_4$-alkylaminocarbonyl-substituted alkyl having 1 to 6 carbon atoms,
  or optionally cyano-, carboxy-, halogen-, C$_1$–C$_4$-alkylcarbonyl-, C$_1$–C$_4$-alkoxycarbonyl- or C$_1$–C$_4$-alkylaminocarbonyl-substituted alkenyl or alkinyl each having 2 to 6 carbon atoms,
  or optionally cyano, carboxy, halogen, C$_1$–C$_4$-alkylcarbonyl- or C$_1$–C$_4$-alkoxycarbonyl-substituted cycloalkyl or cycloalkylalkyl each having 3 to 6 carbon atoms in the cycloalkyl group and optionally 1 to 4 carbon atoms in the alkyl moiety,
  or optionally mono- to tri-hydroxy-, -mercapto-, -amino-, -cyano-, -carboxy-, -carbamoyl-, -thiocarbamoyl-, —C$_1$–C$_4$-alkyl-, —C$_1$–C$_4$-haloalkyl-, —C$_1$–C$_4$-alkoxy-, —C$_1$–C$_4$-haloalkoxy-, —C$_1$–C$_4$-alkylthio-, —C$_1$–C$_4$-haloalkylthio-, —C$_1$–C$_4$-alkylsulphinyl-, —C$_1$–C$_4$-alkylsulphonyl-, —C$_1$–C$_4$-alkylamino- and/or -dimethylamino-substituted aryl or arylalkyl each having 6 or 10 carbon atoms in the aryl group and optionally 1 to 4 carbon atoms in the alkyl moiety,
  or optionally mono- to tri-hydroxy-, -mercapto-, -amino-, -cyano-, -carboxy-, -carbamoyl-, -thiocarbamoyl-, —C$_1$–C$_4$-alkyl-, —C$_1$–C$_4$-haloalkyl-, —C$_1$–C$_4$-alkoxy-, —C$_1$–C$_4$-haloalkoxy-, —C$_1$–C$_4$-alkylthio-, —C$_1$–C$_4$-haloalkylthio-, —C$_1$–C$_4$-alkylsulphinyl-, —C$_1$–C$_4$-alkylsulphonyl-, —C$_1$–C$_4$-alkylamino- and/or -dimethylamino-substituted heterocyclyl or heterocyclylalkyl having 2 to 6 carbon atoms and 1 to 3 nitrogen atoms and/or 1 or 2 oxygen atoms and/or one sulphur atom in the heterocyclyl group and optionally 1 to 4 carbon atoms in the alkyl moiety,
R$^4$ is hydrogen, fluorine, chlorine, bromine or optionally fluorine- and/or chlorine-substituted alkyl having 1 to 6 carbon atoms and
R$^5$ is fluorine- and/or chlorine-substituted alkyl having 1 to 6 carbon atoms.

Particularly preferred definitions of the radicals and groups present in (II) are defined hereinbelow.
R$^1$ is preferably hydrogen, fluorine or chlorine.
R$^2$ is preferably cyano, fluorine, chlorine, bromine, methyl or trifluoromethyl.
R$^3$ is preferably hydroxyl, mercapto, amino, fluorine, chlorine, bromine or one of the radicals —R$^6$, -Q-R$^6$, —NH—R$^6$, —NH—O—R$^6$, —NH—SO$_2$—R$^6$, —N(SO$_2$—R$^6$)$_2$, —CQ$^1$-R$^6$, —CQ$^1$-Q$^2$-R$^6$, —CQ$^1$-NH—R$^6$, Q$^2$-CQ$^1$-R$^6$, —NH—CQ$^1$-R$^6$, —N(SO$_2$—R$^6$)(CQ$^1$-R$^6$), -Q$^2$-CQ$^1$-Q$^2$-R$^6$, —NH—CQ$^1$-Q$^2$-R$^6$ or -Q$^2$-CQ$^1$-NH-R$^6$.
Q is preferably O, S or SO$_2$.
Q$^1$ and Q$^2$ are each independently preferably oxygen.
R$^4$ is preferably hydrogen, fluorine, chlorine, bromine, methyl, ethyl or trifluoromethyl.
R$^5$ is preferably trifluoromethyl, chlorodifluoromethyl, fluorodichloromethyl or pentafluoroethyl.
R$^6$ is preferably optionally cyano-, fluorine-, chlorine-, methoxy-, ethoxy-, methylthio-, ethylthio-, acetyl-, propionyl-, methoxycarbonyl-, ethoxycarbonyl-, methylaminocarbonyl- or ethylaminocarbonyl-substituted methyl, ethyl, n- or i-propyl, n-, i- or s-butyl,
  or optionally cyano-, carboxy-, fluorine-, chlorine-, bromine-, acetyl-, propionyl-, n- or i-butyroyl-, methoxycarbonyl-, ethoxycarbonyl-, n- or i-propoxycarbonyl-, methylaminocarbonyl-, ethylaminocarbonyl-, n- or i-propylaminocarbonyl-substituted propenyl, butenyl, propinyl or butinyl,
  or optionally cyano-, carboxy-, fluorine-, chlorine-, bromine-, acetyl-, propionyl-, methoxycarbonyl- or ethoxycarbonyl-substituted cyclopropyl, cyclobutyl, cyclopentyl, cyclohexyl, cyclopropylmethyl, cyclobutylmethyl, cyclopentylmethyl or cyclohexylmethyl,
  or optionally mono- to tri-hydroxy-, -mercapto-, -amino-, -cyano-, -carboxy-, -carbamoyl-, -thiocarbamoyl-, -methyl-, -ethyl-, -trifluoromethyl-, -methoxy-, -ethoxy-, -difluoromethoxy-, -trifluoromethoxy-, -methylthio-, -ethylthio-, -difluoromethylthio-, -trifluoromethylthio-, -methylsulphinyl-, -ethylsulphinyl-, -methylsulphonyl-, -methylamino-, -ethylamino- and/or -dimethylamino-substituted phenyl, benzyl or phenylethyl,
  or optionally mono- or di-hydroxy-, -mercapto-, -amino-, -cyano-, -carboxy-, -carbamoyl-, -thiocarbamoyl-, -methyl-, -ethyl-, -n- or -i-propyl-, -n-, -i-, -s- or -t-butyl-, -difluoromethyl-, -dichloromethyl-, -trifluoromethyl-, -trichloromethyl-, -chlorodifluoromethyl-, -fluorodichloromethyl-, -methoxy-, -ethoxy-, -difluoromethoxy-, -trifluoromethoxy-, -methylthio-, -ethylthio-, -difluoromethylthio-, -trifluoromethylthio-, -methylsulphinyl-, -ethylsulphinyl-, -methylsulphonyl-, -ethylsulphonyl-, -methylamino-, -ethylamino- and/or -dimethylamino-substituted heterocyclyl or heterocyclylalkyl from the group of oxiranyl, oxetanyl, furyl, tetrahydrofuryl, dioxolanyl, thienyl, tetrahydrothienyl, pyrrolyl, pyrazolyl, imidazolyl, triazolyl, oxazolyl, isoxazolyl, thiazolyl, isothiazolyl, oxadiazolyl, thiadiazolyl, pyridinyl, pyrimidinyl, triazinyl, pyrazolylmethyl, furylmethyl, thienylmethyl, oxazolylmethyl, isoxazolylmethyl, thiazolylmethyl, pyridinylmethyl, pyrimidinylmethyl.
R$^1$ is more preferably hydrogen, fluorine or chlorine.
R$^2$ is more preferably cyano.
R$^3$ is more preferably one of the radicals —NH—R$^6$, —NH—O—R$^6$, NH—SO$_2$—R$^6$-, —NH—CQ$^1$-R$^6$ or —N(SO$_2$—R$^6$)(CQ$^1$-R$^6$).
Q is more preferably O or SO$_2$.
R$^6$ is more preferably optionally fluorine- and/or chlorine-substituted methyl, ethyl or n- or i-propyl,
  or optionally cyano-, fluorine- and/or chlorine-substituted propenyl or butenyl,
  or optionally cyano-, fluorine-, chlorine- or acetyl-substituted cyclopropyl, cyclopentyl, cyclohexyl, cyclopropylmethyl, cyclopentylmethyl or cyclohexylmethyl,
  or optionally mono- to tri-hydroxy-, -carboxy-, -methyl-, -ethyl-, -trifluoromethyl-, -methoxy- or -ethoxy-substituted phenyl, benzyl or phenylethyl,
  or optionally mono- or di-hydroxy-, -amino-, -methyl-, -ethyl-, -trifluoromethyl-, -methoxy- or -ethoxy-substituted heterocyclyl or heterocyclylalkyl from the group of furyl, tetrahydrofuryl, thienyl, tetrahydrothienyl, pyrrolyl, pyrazolyl, imidazolyl, triazolyl, thiazolyl, thiadiazolyl, pyrazolylmethyl, furylmethyl, thienylmethyl or thiazolylmethyl.

The starting materials of the general formula (II) are not yet disclosed by the literature; as novel substances, they also form part of the subject-matter of the present application.

The novel 1-amino-6-hydroxy-3-phenyldihydro-1,4(1H,3H)pyrimidinedione derivatives of the general formula (II)

are obtained when 3-phenyl-2H-1,3-oxazine-2,4-(3H)dione derivatives of the general formula (III)

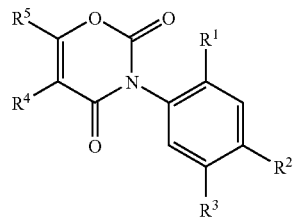

(III)

in which
R¹, R², R³, R⁴ and R⁵ are each as defined above, are reacted with hydrazine, hydrazine hydrate or an acid adduct of hydrazine, for example hydrazine acetate, hydrazine hydrochloride or hydrazine sulphate, preferably with hydrazine hydrate, optionally in the presence of a reaction assistant and/or diluent, for example acetic acid or propionic acid, at temperatures between −30° C. and +100° C., preferably between −10° C. and +80° C.

The 3-phenyl-2H-1,3-oxazine-2,4(3H)dione derivatives of the general formula (III) are known and/or can be prepared by processes known per se (cf. EP-A-371240, EP-A-638563, WO-A-98/27057, WO-A-98/27067, WO-A-98/27068).

The process according to the invention for preparing 1-amino-3-phenyluracil derivatives (1-amino-3-phenyl-2,4 (1H,3H)pyrimidinedione derivatives) of the general formula (I) is carried out with the use of a dehydrating agent. Useful dehydrating agents in this context are the customary water-removing substances. Preferred groups of dehydrating agents are: carbodiimides, e.g. dicyclohexylcarbodiimide, orthoesters, e.g. trimethyl or triethyl orthoformate, acids, e.g. hydrochloric acid, sulphuric acid, methanesulphonic acid, benzenesulphonic acid, p-toluenesulphonic acid or trifluoroacetic acid, acid anhydrides, e.g. acetic anhydride, propionic anhydride, phosphorus(V) oxide or sulphur trioxide, acid chlorides, e.g. phosgen, oxalyl chloride, thionyl chloride, sulphuryl chloride, phosphoryl chloride, phosphorus(V) chloride, diethyl chlorophosphate, acetyl chloride, chlorotrimethylsilane, methanesulphonyl chloride, benzenesulphonyl chloride, p-toluenesulphonyl chloride, or Lewis acids, e.g. boron trifluoride or aluminium trichloride.

Very particular preference is given to using thionyl chloride as the dehydrating agent in the process according to the invention.

The process according to the invention for preparing 1-amino-3-phenyluracil derivatives (1-amino-3-phenyl-2,4 (1H,3H)pyrimidinedione derivatives) of the general formula (I) is carried out using one or more reaction assistants. Useful reaction assistants when carrying out the process according to the invention are all customary inorganic or organic bases. Preference is given to using alkali metal or alkaline earth metal, acetates, amides, carbonates, hydrogen carbonates, hydrides, hydroxides or alkoxides, for example sodium acetate, potassium acetate or calcium acetate, lithium amide, sodium amide, potassium amide or calcium amide, sodium carbonate, potassium carbonate or calcium carbonate, sodium hydrogencarbonate, potassium hydrogencarbonate or calcium hydrogencarbonate, lithium hydride, sodium hydride, potassium hydride or calcium hydride, lithium hydroxide, sodium hydroxide, potassium hydroxide or calcium hydroxide, sodium or potassium methoxide, ethoxide, n- or i-propoxide, n-, i-, s- or t-butoxide; and also basic organic nitrogen compounds, for example trimethylamine, triethylamine, tripropylamine, tributylamine, ethyldiisopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methylpyridine, 4-dimethylaminopyridine, N-methylpiperidine, N-ethylpiperidine, N-methylmorpholine, N-ethylmorpholine, 1,4-diazabicyclo [2,2,2]octane (DABCO), 1,5-diazabicyclo[4,3,0]non-5-ene (DBN), or 1,8-diazabicyclo[5,4,0]undec-7-ene (DBU).

The abovementioned basic organic nitrogen compounds, in particular pyridine, are used with very particular preference as reaction assistants in the process according to the invention.

The process according to the invention for preparing 1-amino-3-phenyluracil derivatives (1-amino-3-phenyl-2,4 (1H,3H)pyrimidinedione derivatives) of the general formula (I) is carried out using one or more diluents. Useful diluents when carrying out the process according to the invention are all customary inert, organic solvents.

Preference is given to using aliphatic, alicyclic or aromatic, optionally halogenated hydrocarbons, for example benzine, benzene, toluene, xylene, chlorobenzene, dichlorobenzene, petroleum ether, hexane, cyclohexane, dichloromethane, chloroform, carbon tetrachloride; ethers such as diethyl ether, diisopropyl ether, dioxane, tetrahydrofuran or ethylene glycol dimethyl or diethyl ether; ketones such as acetone, butanone or methyl isobutyl ketone; nitriles such as acetonitrile, propionitrile or n- or i-butyronitrile; amides such as N,N-dimethylformamide, N,N-diethylformamide, N,N-dipropylformamide, N,N-dibutylformamide, N,N-dimethylacetamide, N-methylformanilide, N-methylpyrrolidone or hexamethylphosphoramide; esters such as methyl acetate or ethyl acetate, sulphoxides such as dimethyl sulphoxide.

Very particular preference is given to using aprotic polar solvents, for example methyl isobutyl ketone, acetonitrile, propionitrile or n- or i-butyronitrile, N,N-dimethylformamide or N,N-dimethylacetamide, as diluents in the process according to the invention.

When carrying out the process according to the invention for preparing compounds of the formula (I), the reaction temperatures can be varied within a relatively wide range. The working temperatures are generally between −30° C. and +180° C., preferably between −10° C. and +150° C., more preferably between 0° C. and 100° C.

The process according to the invention is generally carried out working under atmospheric pressure. However, it is also possible to work under elevated pressure or, as long as no volatile components are used, under reduced pressure.

To carry out the process according to the invention, generally between 0.2 and 2 mol, preferably between 0.5 and 1.5 mol, of a dehydrating agent are used per mole of 1-amino-6-hydroxy-3-phenyldihydro-2,4(1H,3H)pyrimidinedione derivative of the formula (II).

In a preferred embodiment of the process according to the invention, the amino-6-hydroxy-3-phenyldihydro-2,4(1H, 3H)pyrimidinedione derivative of the formula (II) is initially charged in a suitable diluent, and the dehydrating agent and also reaction assistants are metered in slowly. The reaction mixture is then stirred, optionally at elevated temperature, up to the end of the reaction. The workup is effected by customary methods (cf. the preparation examples).

The 1-amino-3-phenyluracil derivatives of the formula (I) can be used as herbicides for controlling weeds (cf. EP-A-648 749, WO-A-94/04511, WO-A-95/29168, WO-A-96/35679).

PREPARATION EXAMPLES

Example 1

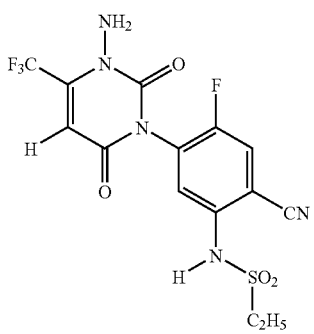

25.5 g (97.5%, 56.7 mMol) of N-[5-(3-amino-4-hydroxy-2,6-dioxo-4-trifluoromethyl-tetrahydro-1(2H)-pyrimidinyl)-2-cyano-4-fluorophenyl]ethanesulphonamide are initially charged in 100 ml of n-butyronitrile and 224 mg (2.8 mMol) of pyridine are added at room temperature (approx. 20° C.). 33.7 g of thionyl chloride are added dropwise to the suspension. Slight gas evolution takes place and the reaction mixture becomes yellow. After about a minute, a clear solution has formed, cloudiness sets in after about 5 minutes and a voluminous precipitate has formed after about 10 minutes. The mixture is heated to reflux temperature and stirred for a further 30 minutes, and significant gas evolution sets in above about 60° C. After cooling to room temperature, the mixture is diluted with 50 ml of n-butyronitrile, 100 ml of ice-water are added, the phases are separated, and the organic phase is washed three times with a little water, dried over sodium sulphate and filtered. The solvent is carefully distilled off from the filtrate under reduced pressure.

22.6 g (94% according to 19F NMR quantification, 89% of theory) of N-[5-(3-amino-2,6-dioxo-4-trifluoromethyl-3,6-dihydro-1(2H)-pyrimidinyl)-2-cyano-4-fluorophenyl]ethanesulphonamide of melting point 190° C. are obtained.

Starting Materials of the Formula (II)

Example (II-1)

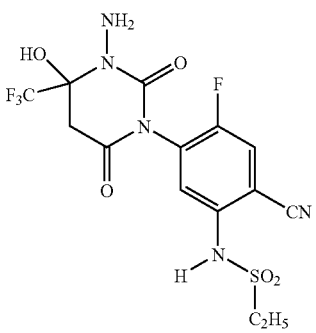

60.7 g (99.3%, 150 mmol) of N-[2-cyano-5-(2,4-dioxo-6-trifluoromethyl-2H-1,3-oxazin-3(4H)-yl)-4-fluorophenyl]ethanesulphonamide are initially charged in 300 ml of propionic acid, and 9.0 g of hydrazine hydrate (99%, 178 mmol) are added with stirring at room temperature (approx. 20° C.). The mixture (suspension) heats to approx. 30° C. and the suspension is stirred at this temperature for 5 hours, while the colour lightens. The mixture is then cooled to 15° C. and filtered with suction, and the filter residue is triturated with a spatula on the suction filter and washed repeatedly with isopropanol and sucked to dryness. The slightly yellowish filtercake is initially dried under air and then overnight in a desiccator over potassium hydroxide.

41 g (94.9%, 60% of theory) of N-[5-(3-amino-4-hydroxy-2,6-dioxo-4-trifluoromethyltetrahydro-1(2H)-pyrimidinyl)-2-cyano-4-fluorophenyl]ethanesulphonamide having a melting point of 182° C. (decomposition) are obtained.

After concentrating the mother liquor, the residue, according to HPLC analysis, still contains 35.5% of N-[5-(3-amino-4-hydroxy-2,6-dioxo-4-trifluoromethyltetrahydro-1(2H)-pyrimidinyl)-2-cyano-4-fluorophenyl]ethanesulphonamide (corresponds to a further 23% of the theoretical yield). This therefore results in a total yield of 83% of theory.

What is claimed is:

1. A process for preparing a compound of formula (I)

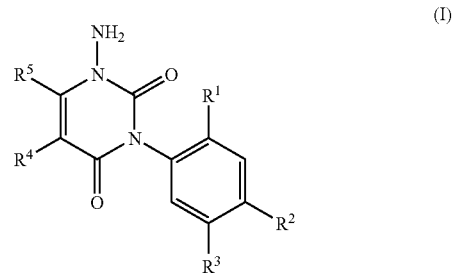

in which is hydrogen, cyano, nitro, or halogen, $R^2$ is cyano, nitro, halogen, or optionally substituted alkyl or alkoxy, $R^3$ is hydrogen, hydroxyl, mercapto, amino, hydroxyamino, hydrazino, halogen, or one of the radicals —$R^6$, -Q-$R^6$, —NH—$R^6$, —NH—O—$R^6$, —NH—SO$_2$—$R^6$, —N(SO$_2$—$R^6$)$_2$, —CQ$^1$-$R^6$, —CQ$^1$-Q$^2$-$R^6$, —CQ$^1$-NH—$R^6$, -Q$^2$-CQ$^1$-$R^6$, —NH—CQ$^1$-$R^6$, —N(SO$_2$—$R^6$)(CQ$^1$-$R^6$), -Q$^2$-CQ$^1$-Q$^2$-$R^6$, —NH—CQ$^1$-Q$^2$-$R^6$, or -Q$^2$-CQ$^1$-NH—$R^6$, where Q is O, S, SO, or SO$_2$, $Q^1$ and $Q^2$ are each independently oxygen or sulphur, and $R^6$ is optionally substituted alkyl, alkenyl, alkynyl, cycloalkyl, cycloalkylalkyl, aryl, arylalkyl, heterocyclyl, or heterocyclylalkyl, $R^4$ is hydrogen, halogen, or optionally substituted alkyl, and $R^5$ is fluorine- and/or chlorine-substituted alkyl, comprising reacting a compound of formula (II)

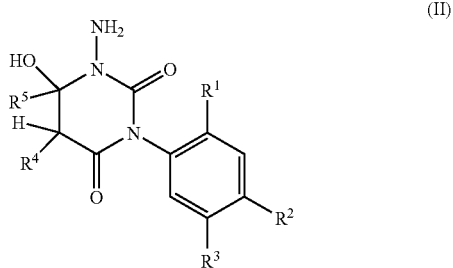

in which $R^1$, $R^2$, $R^3$, $R^4$, and $R^5$ are each as defined for formula (I), with a dehydrating agent at temperatures between −30° C. and +180° C.

2. A process according to claim 1 wherein for the compound of formula (II), $R^1$ is hydrogen, cyano, nitro, fluorine, chlorine, or bromine, $R^2$ is cyano, nitro, fluorine, chlorine, bromine, or optionally fluorine- and/or chlorine-substituted alkyl or alkoxy having 1 to 4 carbon atoms, $R^3$ is hydrogen, hydroxyl, mercapto, amino, hydroxyamino, halogen, or one of the radicals —$R^6$, -Q-$R^6$, —NH—$R^6$, —NH—O—$R^6$, —NH—$SO_2$—$R^6$, —N($SO_2$—$R^6$)$_2$, —$CQ^1$-$R^6$, —$CQ^1$-$Q^2$-$R^6$, —$CQ^1$-NH—$R^6$, -$Q^2$-$CQ^1$-$R^6$, —NH—$CQ^1$-$R^6$, —N($SO_2$—$R^6$)($CQ^1$-$R^6$), -$Q^2$-$CQ^1$-$Q^2$-$R^6$, —NH—$CQ^1$-$Q^2$-$R^6$, or -$Q^2$-$CQ^1$-NH—$R^6$, where Q is O, S, SO, or $SO_2$, $Q^1$ and $Q^2$ are each independently oxygen or sulphur, and $R^6$ is optionally cyano-, halogen-, $C_1$–$C_4$-alkoxy-, $C_1$–$C_4$-alkylthio-, $C_1$–$C_4$-alkylcarbonyl-, $C_1$–$C_4$-alkoxycarbonyl-, or $C_1$–$C_4$-alkylaminocarbonyl-substituted alkyl having 1 to 6 carbon atoms; or optionally cyano-, carboxy-, halogen-, $C_1$–$C_4$-alkylcarbonyl-, $C_1$–$C_4$-alkoxycarbonyl-, or $C_1$–$C_4$-alkylaminocarbonyl-substituted alkenyl or alkynyl each having 2 to 6 carbon atoms; or optionally cyano, carboxy, halogen, $C_1$–$C_4$-alkylcarbonyl- or $C_1$–$C_4$-alkoxycarbonyl-substituted cycloalkyl or cycloalkylalkyl each having 3 to 6 carbon atoms in the cycloalkyl group and 1 to 4 carbon atoms in the alkyl moiety; or optionally mono- to trihydroxy-, -mercapto-, -amino-, -cyano-, -carboxy-, -carbamoyl-, -thiocarbamoyl-, —$C_1$–$C_4$-alkyl-, —$C_1$–$C_4$-haloalkyl-, —$C_1$–$C_4$-alkoxy-, —$C_1$–$C_4$-haloalkoxy-, —$C_1$–$C_4$-alkylthio-, —$C_1$–$C_4$-haloalkylthio-, —$C_1$–$C_4$-alkylsulphinyl-, —$C_1$–$C_4$-alkylsulphonyl-, —$C_1$–$C_4$-alkylamino-, and/or -dimethylamino-substituted aryl or arylalkyl each having 6 or 10 carbon atoms in the aryl group and 1 to 4 carbon atoms in the alkyl moiety; or optionally mono- to tri-hydroxy-, -mercapto-, -amino-, -cyano-, -carboxy-, -carbamoyl-, -thiocarbamoyl-, —$C_1$–$C_4$-alkyl-, —$C_1$–$C_4$-haloalkyl-, —$C_1$–$C_4$-alkoxy-, —$C_1$–$C_4$-haloalkoxy-, —$C_1$–$C_4$-alkylthio-, —$C_1$–$C_4$-haloalkythio-, —$C_1$–$C_4$-alkylsulphinyl-, —$C_1$–$C_4$-alkylsulphonyl-, —$C_1$–$C_4$-alkylamino-, and/or dimethylamino-substituted heterocyclyl or heterocyclylalkyl having 2 to 6 carbon atoms and 1 to 3 nitrogen atoms and/or 1 or 2 oxygen atoms and/or one sulphur atom in the heterocyclyl group and 1 to 4 carbon atoms in the alkyl moiety, $R^4$ is hydrogen, fluorine, chlorine, bromine, or optionally fluorine- and/or chlorine-substituted alkyl having 1 to 6 carbon atoms, and $R^5$ is fluorine- and/or chlorine-substituted alkyl having 1 to 6 carbon atoms.

3. A process according to claim 1 wherein for the compound of formula (II), $R^1$ is hydrogen, fluorine, or chlorine, $R^2$ is cyano, fluorine, chlorine, bromine, methyl, or trifluoromethyl, $R^3$ is hydroxyl, mercapto, amino, fluorine, chlorine, bromine, or one of the radicals —$R^6$, -Q-$R^6$, —NH—$R^6$, —NH—O—$R^6$, —NH—$SO_2$—$R^6$, —N($SO_2$—$R^6$)$_2$, —$CQ^1$-$R^6$, —$CQ^1$-$Q^2$-$R^6$, —$CQ^1$-NH—$R^6$, -$Q^2$-$CQ^1$-$R^6$, —NH—$CQ^1$-$R^6$, —N($SO_2$—$R^6$)($CQ^1$-$R^6$), -$Q^2$-$CQ^1$-$Q^2$-$R^6$, —NH—$CQ^1$-$Q^2$-$R^6$, or -$Q^2$-$CQ^1$-NH-$R^6$, where Q is O, S, SO, or $SO_2$, $Q^1$ and $Q^2$ are each independently oxygen or sulphur, and $R^6$ is optionally cyano-, fluorine-, chlorine-, methoxy-, ethoxy-, methylthio-, ethylthio-, acetyl-, propionyl-, methoxycarbonyl-, ethoxycarbonyl-, methylaminocarbonyl-, or ethylaminocarbonyl-substituted methyl, ethyl, n- or i-propyl, or n-, i-, or s-butyl; or optionally cyano-, carboxy-, fluorine-, chlorine-, bromine-, acetyl-, propionyl-, n- or i-butyroyl-, methoxycarbonyl-, ethoxycarbonyl-, n- or i-propoxycarbonyl-, methylaminocarbonyl-, ethylaminocarbonyl-, or n- or i-propylaminocarbonyl-substituted propenyl, butenyl, propynyl, or butynyl; or optionally cyano-, carboxy-, fluorine-, chlorine-, bromine-, acetyl-, propionyl-, methoxycarbonyl-, or ethoxycarbonyl-substituted cyclopropyl, cyclobutyl, cyclopentyl, cyclohexyl, cyclopropylmethyl, cyclobutylmethyl, cyclopentylmethyl, or cyclohexylmethyl; or optionally mono- to trihydroxy-, -mercapto-, -amino-, -cyano-, -carboxy-, -carbamoyl-, -thiocarbamoyl-, -methyl-, -ethyl-, -trifluoromethyl-, -methoxy-, -ethoxy-, -difluoromethoxy-, -trifluoromethoxy-, -methylthio-, -ethylthio-, -difluoromethylthio-, -trifluoromethylthio-, -methylsulphinyl-, -ethylsulphinyl-, -methylsulphonyl-, -methylamino-, -ethylamino-, and/or -dimethylamino-substituted phenyl, benzyl, or phenylethyl; or optionally mono- or dihydroxy-, -mercapto-, -amino-, -cyano-, -carboxy-, -carbamoyl-, -thiocarbamoyl-, -methyl-, -ethyl-, -n- or -i-propyl-, -n-, -i-, -s-, or -t-butyl-, -difluoromethyl-, -dichloromethyl-, -trifluoromethyl-, -trichloromethyl-, -chlorodifluoromethyl-, -fluorodichloromethyl-, -methoxy-, -ethoxy-, -difluoromethoxy-, -trifluoromethoxy-, -methylthio-, -ethylthio-, -difluoromethylthio-, -trifluoromethylthio-, -methylsulphinyl-, -ethylsulphinyl-, -methylsulphonyl-, -ethylsulphonyl-, -methylamino-, -ethylamino-, and/or -dimethylamino-substituted heterocyclyl or heterocyclylalkyl selected from the group consisting of oxiranyl, oxetanyl, furyl, tetrahydrofuryl, dioxolanyl, thienyl, tetrahydrothienyl, pyrrolyl, pyrazolyl, imidazolyl, triazolyl, oxazolyl, isoxazolyl, thiazolyl, isothiazolyl, oxadiazolyl, thiadiazolyl, pyridinyl, pyrimidinyl, triazinyl, pyrazolylmethyl, furylmethyl, thienylmethyl, oxazolylmethyl, isoxazolylmethyl, thiazolylmethyl, pyridinylmethyl, and pyrimidinylmethyl, $R^4$ is hydrogen, fluorine, chlorine, bromine, methyl, ethyl, or trifluoromethyl, and $R^5$ is trifluoromethyl, chlorodifluoromethyl, fluorodichloromethyl, or pentafluoroethyl.

4. A compound of formula (II)

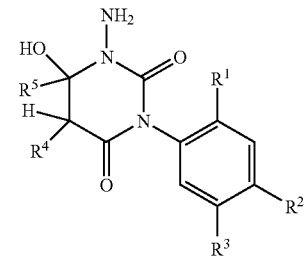

(II)

in which $R^1$ is hydrogen, cyano, nitro, or halogen, $R^2$ is cyano, nitro, halogen, or optionally substituted alkyl or alkoxy, $R^3$ is hydrogen, hydroxyl, mercapto, amino, hydroxyamino, hydrazino, halogen, or one of the radicals —$R^6$, -Q-$R^6$, —NH—$R^6$, —NH—O—$R^6$, —NH—SO$_2$—$R^6$, —N(SO$_2$—$R^6$)$_2$, —CQ$^1$-$R^6$, —CQ$^1$-Q$^2$-$R^6$, —CQ$^1$-NH—$R^6$, -Q$^2$-CQ$^1$-$R^6$, —NH—CQ$^1$-$R^6$, —N(SO$_2$—$R^6$)(CQ$^1$-$R^6$), -Q$^2$-CQ$^1$-Q$^2$-$R^6$, —NH—CQ$^1$-Q$^2$-$R^6$, or -Q$^2$-CQ$^1$-NH—$R^6$, where Q is O, S, SO, or SO$_2$, Q$^1$ and Q$^2$ are each independently oxygen or sulphur, and $R^6$ is optionally substituted alkyl, alkenyl, alkynyl, cycloalkyl, cycloalkylalkyl, aryl, arylalkyl, heterocyclyl, or heterocyclylalkyl, $R^4$ is hydrogen, halogen, or optionally substituted alkyl, and $R^5$ is fluorine- and/or chlorine-substituted alkyl.

5. A compound of formula (II) according to claim 4 in which $R^1$ is hydrogen, cyano, nitro, fluorine, chlorine, or bromine, $R^2$ is cyano, nitro, fluorine, chlorine, bromine, or optionally fluorine- and/or chlorine-substituted alkyl or alkoxy having 1 to 4 carbon atoms, $R^3$ is hydrogen, hydroxyl, mercapto, amino, hydroxyamino, halogen, or one of the radicals —$R^6$, -Q-$R^6$, —NH—$R^6$, —NH—O—$R^6$, —NH—SO$_2$—$R^6$, —N(SO$_2$—$R^6$)$_2$, —CQ$^1$-$R^6$, —CQ$^1$-Q$^2$-$R^6$, —CQ$^1$-NH—$R^6$, -Q$^2$-CQ$^1$-$R^6$, —NH—CQ$^1$-$R^6$, —N(SO$_2$—$R^6$)(CQ$^1$-$R^6$), -Q$^2$-CQ$^1$-Q$^2$-$R^6$, —NH—CQ$^1$-Q$^2$-$R^6$, or -Q$^2$-CQ$^1$-NH—$R^6$, where Q is O, S, SO, or SO$_2$, Q$^1$ and Q$^2$ are each independently oxygen or sulphur, and $R^6$ is optionally cyano-, halogen-, $C_1$–$C_4$-alkoxy-, $C_1$–$C_4$-alkylthio-, $C_1$–$C_4$-alkylcarbonyl-, $C_1$–$C_4$-alkoxycarbonyl-, or $C_1$–$C_4$-alkylaminocarbonyl-substituted alkyl having 1 to 6 carbon atoms; or optionally cyano-, carboxy-, halogen-, $C_1$–$C_4$-alkylcarbonyl-, $C_1$–$C_4$-alkoxycarbonyl-, or $C_1$–$C_4$-alkylaminocarbonyl-substituted alkenyl or alkynyl each having 2 to 6 carbon atoms; or optionally cyano, carboxy, halogen, $C_1$–$C_4$-alkylcarbonyl- or $C_1$–$C_4$-alkoxycarbonyl-substituted cycloalkyl or cycloalkylalkyl each having 3 to 6 carbon atoms in the cycloalkyl group and 1 to 4 carbon atoms in the alkyl moiety; or optionally mono- to trihydroxy-, -mercapto-, -amino-, -cyano-, -carboxy-, -carbamoyl-, -thiocarbamoyl-, —$C_1$–$C_4$-alkyl-, —$C_1$–$C_4$-haloalkyl-, —$C_1$–$C_4$-alkoxy-, —$C_1$–$C_4$-haloalkoxy-, —$C_1$–$C_4$-alkylthio-, —$C_1$–$C_4$-haloalkylthio-, —$C_1$–$C_4$-alkylsulphinyl-, —$C_1$–$C_4$-alkylsulphonyl-, —$C_1$–$C_4$-alkylamino-, and/or -dimethylamino-substituted aryl or arylalkyl each having 6 or 10 carbon atoms in the aryl group and 1 to 4 carbon atoms in the alkyl moiety; or optionally mono- to tri-hydroxy-, -mercapto-, -amino-, -cyano-, -carboxy-, -carbamoyl-, -thiocarbamoyl-, —$C_1$–$C_4$-alkyl-, —$C_1$–$C_4$-haloalkyl-, —$C_1$–$C_4$-alkoxy-, —$C_1$–$C_4$-haloalkoxy-, —$C_1$–$C_4$-alkylthio-, —$C_1$–$C_4$-haloalkylthio-, —$C_1$–$C_4$-alkylsulphinyl-, —$C_1$–$C_4$-alkylsulphonyl-, —$C_1$–$C_4$-alkylamino-, and/or dimethylamino-substituted heterocyclyl or heterocyclylalky having 2 to 6 carbon atoms and 1 to 3 nitrogen atoms and/or 1 or 2 oxygen atoms and/or one sulphur atom in the heterocyclyl group and 1 to 4 carbon atoms in the alkyl moiety, $R^4$ is hydrogen, fluorine, chlorine, bromine, or optionally fluorine- and/or chlorine-substituted alkyl having 1 to 6 carbon atoms, and $R^5$ is fluorine- and/or chlorine-substituted alkyl having 1 to 6 carbon atoms.

6. A compound of formula (II) according to claim 4 in which $R^1$ is hydrogen, fluorine, or chlorine, $R^2$ is cyano, fluorine, chlorine, bromine, methyl, or trifluoromethyl, $R^3$ is hydroxyl, mercapto, amino, fluorine, chlorine, bromine, or one of the radicals —$R^6$, -Q-$R^6$, —NH—$R^6$, —NH—O—$R^6$, —NH—SO$_2$—$R^6$, —N(SO$_2$—$R^6$)$_2$, —CQ$^1$-$R^6$, —CQ$^1$-Q$^2$-$R^6$, —CQ$^1$-NH—$R^6$, -Q$^2$-CQ$^1$-$R^6$, —NH—CQ$^1$-$R^6$, —N(SO$_2$—$R^6$)(CQ$^1$-$R^6$), -Q$^2$-CQ$^1$-Q$^2$-$R^6$, —NH—CQ$^1$-Q$^2$-$R^6$, or -Q$^2$-CQ$^1$-NH—$R^6$, where Q is O, S, SO, or SO$_2$, Q$^1$ and Q$^2$ are each independently oxygen or sulphur, and $R^6$ is optionally cyano-, fluorine-, chlorine-, methoxy-, ethoxy-, methylthio-, ethylthio-, acetyl-, propionyl-, methoxycarbonyl-, ethoxycarbonyl-, methylaminocarbonyl-, or ethylaminocarbonyl-substituted methyl, ethyl, n- or i-propyl, or n-, i-, or s-butyl; or optionally cyano-, carboxy-, fluorine-, chlorine-, bromine-, acetyl-, propionyl-, n- or i-butyroyl-, methoxycarbonyl-, ethoxycarbonyl-, n- or i-propoxycarbonyl-, methylaminocarbonyl-, ethylaminocarbonyl-, or n- or -propylaminocarbonyl-substituted propenyl, butenyl, propynyl, or butynyl; or optionally cyano-, carboxy-, fluorine-, chlorine-, bromine-, acetyl-, propionyl-, methoxycarbonyl-, or ethoxycarbonyl-substituted cyclopropyl, cyclobutyl, cyclopentyl, cyclohexyl, cyclopropylmethyl, cyclobutylmethyl, cyclopentylmethyl, or cyclohexylmethyl; or optionally mono- to trihydroxy-, -mercapto-, -amino-, -cyano-, -carboxy-, -carbamoyl-, -thiocarbamoyl-, -methyl-, -ethyl-, -trifluoromethyl-, -methoxy-, -ethoxy-, -difluoromethoxy-, -trifluoromethoxy-, -methylthio-, -ethylthio-, -difluoromethylthio-, -trifluoromethylthio-, -methylsulphinyl-, -ethylsulphinyl-, -methylsulphonyl-, -methylamino-, -ethylamino-, and/or -dimethylamino-substituted phenyl, benzyl, or phenylethyl; or optionally mono- or di-hydroxy-, -mercapto-, -amino-, -cyano-, -carboxy-, -carbamoyl-, -thiocarbamoyl-, -methyl-, -ethyl-, -n- or -i-propyl-, -n-, -i-, -s-, or -t-butyl-, -difluoromethyl-, -dichloromethyl-, -trifluoromethyl-, -trichloromethyl-, -chlorodifluoromethyl-, -fluorodichloromethyl-, -methoxy-, -ethoxy-, -difluoromethoxy-, -trifluoromethoxy-, -methylthio-, -ethylthio-, -difluoromethylthio-, -trifluoromethylthio-, -methylsulphinyl-, -ethylsulphinyl-, -methylsulphonyl-, -ethylsulphonyl-, -methylamino-, -ethylamino-, and/or -dimethylamino-substituted heterocyclyl or heterocyclylalkyl selected from the group consisting of oxiranyl, oxetanyl, furyl, tetrahydrofuryl, dioxolanyl, thienyl, tetrahydrothienyl, pyrrolyl, pyrazolyl, imidazolyl, triazolyl, oxazolyl, isoxazolyl, thiazolyl, isothiazolyl, oxadiazolyl, thiadiazolyl, pyridinyl, pyrimidinyl, triazinyl, pyrazolylmethyl, furylmethyl thienylmethyl, oxazolylmethyl, isoxazolylmethyl, thiazolylmethyl, pyridinylmethyl, and pyrimidinylmethyl, $R^4$ is hydrogen, fluorine, chlorine, bromine, methyl, ethyl, or trifluoromethyl, and $R^5$ is trifluoromethyl, chlorodifluoromethyl, fluorodichloromethyl, or pentafluoroethyl.

7. A process for preparing a compound of formula (II) according to claim 4 comprising reacting a compound of formula (III)

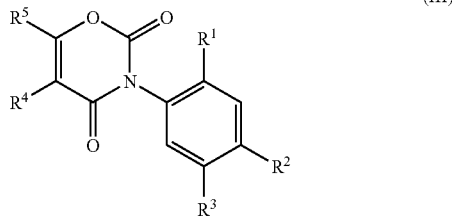

in which $R^1$, $R^2$, $R^3$, $R^4$, and $R^5$ are each as defined for formula (II) in claim 4, with hydrazine, hydrazine hydrate, or an acid adduct of hydrazine at temperatures between −30° C. and +100° C.

8. A process according to claim 1 carried out in the presence of one or more reaction assistants.

9. A process according to claim 1 carried out in the presence of one or more diluents.

10. A process according to claim 9 wherein the diluent is an aprotic polar solvent.

11. A process according to claim 8 carried out in the presence of one or more diluents.

12. A process according to claim 11 wherein the diluent is an aprotic polar solvent.

13. A process according to claim 1 wherein the dehydrating agent is a carbodiimide, orthoester, acid, acid anhydride, acid chloride, or Lewis acid.

14. A process according to claim 1 wherein the dehydrating agent is thionyl chloride.

15. A process according to claim 8 wherein the reaction assistant is a basic organic nitrogen compound.

16. A process according to claim 8 wherein the reaction assistant is pyridine.

17. A process according to claim 1 carried out at temperatures between −10° C. and +150° C.

* * * * *